(12) United States Patent
Adachi

(10) Patent No.: US 10,750,110 B2
(45) Date of Patent: Aug. 18, 2020

(54) ENDOSCOPE SYSTEM AND SIGNAL PROCESSOR TO DETERMINE A SHORT OR AN OPEN CLOCK SIGNAL WIRE

(71) Applicant: OLYMPUS CORPORATION, Tokyo (JP)

(72) Inventor: Fumiyuki Adachi, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/208,655

(22) Filed: Dec. 4, 2018

(65) Prior Publication Data

US 2019/0116332 A1    Apr. 18, 2019

Related U.S. Application Data

(63) Continuation of application No. PCT/JP2017/006179, filed on Feb. 20, 2017.

(30) Foreign Application Priority Data

Aug. 2, 2016 (JP) .................................. 2016-152260

(51) Int. Cl.
*A61B 1/00* (2006.01)
*H04N 5/369* (2011.01)
(Continued)

(52) U.S. Cl.
CPC ....... *H04N 5/3765* (2013.01); *A61B 1/00006* (2013.01); *A61B 1/00018* (2013.01);
(Continued)

(58) Field of Classification Search
CPC ............... H04N 5/3765; H04N 5/3698; H04N 2005/2255; G02B 23/24; G02B 23/2484;
(Continued)

(56) References Cited

U.S. PATENT DOCUMENTS 7,593,051 B2 * 9/2009 Suda ...................... H04N 5/335
348/311
2005/0119527 A1 6/2005 Banik et al.
(Continued)

FOREIGN PATENT DOCUMENTS

| EP | 2266452 A2 | 12/2010 |
| JP | 2006095330 A | 4/2006 |
| JP | 2008514381 A | 5/2008 |
| JP | 2009045113 A | 3/2009 |
| JP | 2009201541 A | 9/2009 |
| WO | 2004086957 A2 | 10/2004 |

OTHER PUBLICATIONS

International Search Report dated May 9, 2017 issued in PCT/JP2017/006179.

*Primary Examiner* — Susan E. Hodges
(74) *Attorney, Agent, or Firm* — Scully, Scott, Murphy & Presser, P.C.

(57) ABSTRACT

An endoscope includes a cable in which a first clock signal wire and a second clock signal wire are provided inside and a differential clock signal receiving section for clocks to be supplied to an image pickup device, and a video processor includes a current detector inserted in VCCI/O for the differential clock signal receiving section, a differential signal output section configured to perform conversion into two differential clock signals, respective phases of the two differential clock signals being reverse of each other, and output the two differential clock signals, and an FPGA configured to, based on a current value detected by the current detector, determine a short or an open in the first clock signal wire and the second clock signal wire.

15 Claims, 11 Drawing Sheets

(51) Int. Cl.
*H04N 7/18* (2006.01)
*H04N 5/376* (2011.01)
*G02B 23/24* (2006.01)
*A61B 1/045* (2006.01)
*H04N 5/225* (2006.01)

(52) U.S. Cl.
CPC .............. *A61B 1/045* (2013.01); *G02B 23/24* (2013.01); *G02B 23/2484* (2013.01); *H04N 5/3698* (2013.01); *H04N 2005/2255* (2013.01)

(58) Field of Classification Search
CPC .. A61B 1/045; A61B 1/00018; A61B 1/00006
USPC ........................................................ 348/70
See application file for complete search history.

(56) References Cited

U.S. PATENT DOCUMENTS

| | | | | |
|---|---|---|---|---|
| 2008/0027284 | A1* | 1/2008 | Suda | A61B 1/00055 |
| | | | | 600/134 |
| 2011/0087217 | A1* | 4/2011 | Yates | A61B 18/1206 |
| | | | | 606/39 |
| 2012/0178992 | A1* | 7/2012 | Fujimoto | A61B 1/00006 |
| | | | | 600/109 |
| 2015/0265347 | A1* | 9/2015 | Yates | A61B 18/18 |
| | | | | 606/50 |
| 2015/0374204 | A1* | 12/2015 | Tabuchi | A61B 1/04 |
| | | | | 600/109 |

* cited by examiner

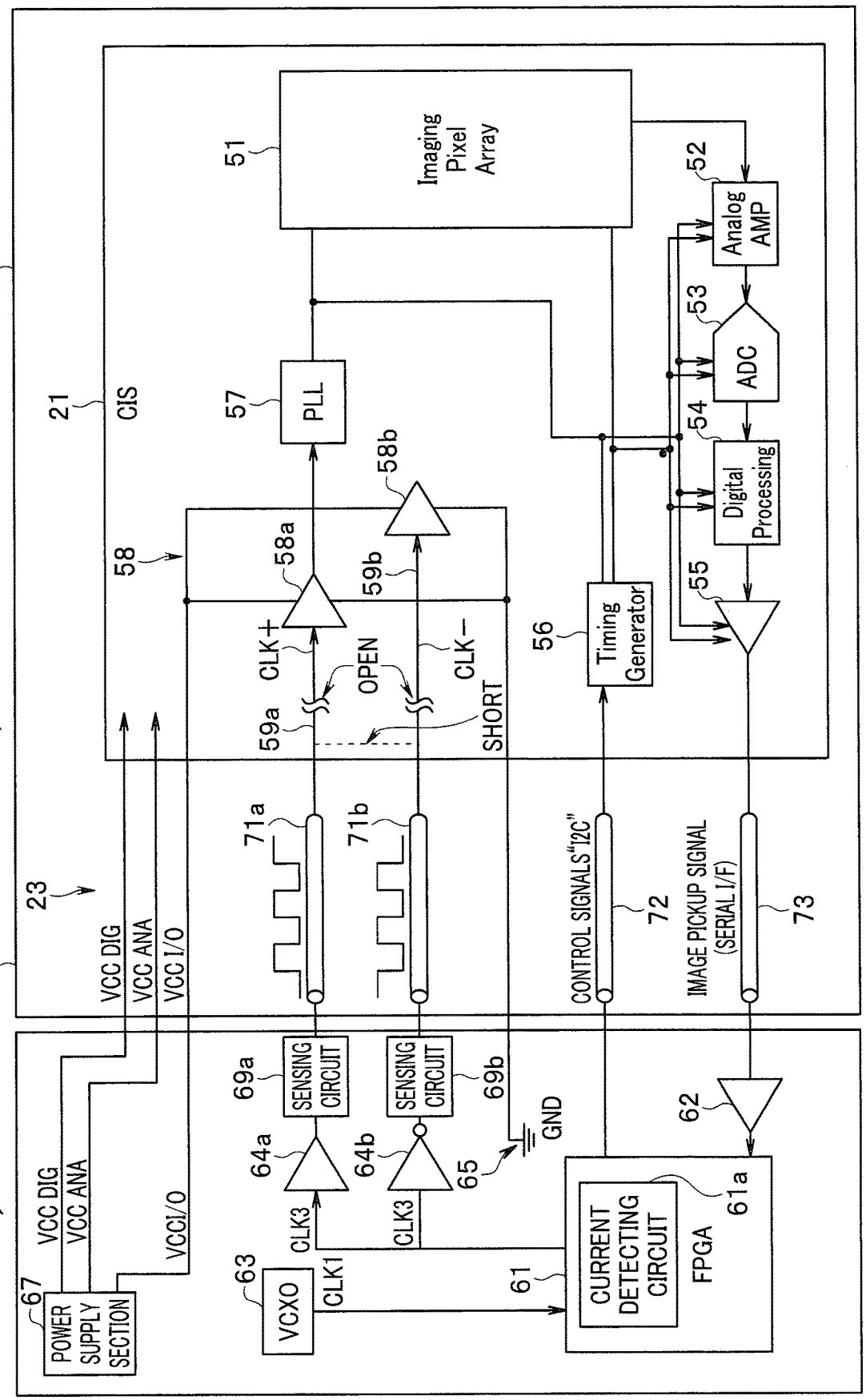

ENDOSCOPE SYSTEM AND SIGNAL PROCESSOR TO DETERMINE A SHORT OR AN OPEN CLOCK SIGNAL WIRE

CROSS REFERENCE TO RELATED APPLICATION

This application is a continuation application of PCT/JP2017/006179 filed on Feb. 20, 2017 and claims benefit of Japanese Application No. 2016-152260 filed in Japan on Aug. 2, 2016, the entire contents of which are incorporated herein by this reference.

BACKGROUND OF THE INVENTION

Field of the Invention

The present invention relates to an endoscope system and a signal processing apparatus and relates to an endoscope system including an endoscope including a solid-state image pickup device driven by a predetermined clock signal, and a signal processing apparatus connected to the endoscope.

Description of the Related Art

Endoscope systems each including, e.g., an endoscope configured to pick up an image of an object inside a subject and an image processing apparatus (signal processing apparatus) configured to generate an observation image of the object picked up by the endoscope have widely been used in a medical field, an industrial field, and the like.

As the endoscope in such an endoscope system above, an endoscope employing a solid-state image pickup device (for example, a CMOS image sensor) driven by a predetermined clock signal and including a cable disposed inside, the cable being configured to transmit an image pickup signal outputted from the solid-state image pickup device, has conventionally been known.

In general, this type of endoscope includes an image pickup device such as above in a distal end portion of an insertion portion. Also, as for clocks supplied to the image pickup device, for example, clocks are supplied to the image pickup device from an external signal processing apparatus via a cable inside the endoscope.

Here, as for the supply of clocks from the signal processing apparatus to the image pickup device, an example in which clocks are transmitted by means of what is called differential signals, via the cable has been known. Inside the cable, power supply channels of various types of power supply from the signal processing apparatus to the image pickup device (for example, a digital power supply channel VCCDIG, an analog power supply channel VCCANA and an I/O power supply channel VCCIO) are provided (see FIGS. 10 and 11).

Furthermore, in recent years, an example in which as an image pickup device in an endoscope, a CMOS (complementary metal-oxide semiconductor) image sensor is employed has been proposed (Japanese Patent Application Laid-Open Publication No. 2006-095330).

In an endoscope system 901, which is illustrated in FIG. 10, an overcurrent sensing circuit 68 is provided on the signal processing apparatus 903 side, which is connected to an endoscope 902, to detect a shorted state in a power supply channel.

Also, an endoscope system 911, which is illustrated in FIG. 11, has a configuration in which sensing circuits (detection sections) 69a, 69b are provided in respective clock signal transmission channels on the signal processing apparatus 913 side, which is connected to an endoscope 912.

SUMMARY OF THE INVENTION

An endoscope system according to an aspect of the present invention includes: an endoscope including an image pickup device configured to be driven by a predetermined clock, a clock receiving circuit configured to receive two differential clock signals transmitted from external signal wires, a first clock signal wire configured to transmit a first differential clock signal that is one signal of the two differential clock signals, and a second clock signal wire configured to transmit a second differential clock signal that is another signal of the two differential clock signals; and a signal processing apparatus including a power supply configured to supply drive power to the clock receiving circuit via a predetermined power supply channel, a current detecting circuit configured to detect a current value relating to the drive power supplied to the clock receiving circuit from the power supply via the power supply channel, a differential signal output circuit configured to receive an input of a generated clock signal, convert the clock signal into the two differential clock signals, phases of the two differential clock signals being reverse of each other, and output the two differential clock signals, and a failure mode determining apparatus configured to, based on the current value detected by the current detecting circuit, determine a failure state relating to at least one of the first clock signal wire and the second clock signal wire in the endoscope.

A signal processing apparatus according to an aspect of the present invention is a signal processing apparatus allowing an endoscope to be connected to the signal processing apparatus, the endoscope including an image pickup device configured to be driven by a predetermined clock, a clock receiving circuit configured to receive two differential clock signals transmitted from external signal wires, a first clock signal wire configured to transmit a first differential clock signal that is one signal of the two differential clock signals, and a second clock signal wire configured to transmit a second differential clock signal that is another signal of the two differential clock signals, the signal processing apparatus including: a power supply configured to supply drive power to the clock receiving circuit via a predetermined power supply channel; a current detecting circuit configured to detect a current value relating to the drive power supplied to the clock receiving circuit from the power supply via the power supply channel; a differential signal output circuit configured to receive an input of a generated clock signal, convert the clock signal into the two differential clock signals, phases of the two differential clock signals being reverse of each other, and output the two differential clock signals; and a failure mode determining apparatus configured to, based on the current value detected by the current detecting circuit, determine a failure state relating to at least one of the first clock signal wire and the second clock signal wire in the endoscope.

BRIEF DESCRIPTION OF THE DRAWINGS

FIG. 11 is a block diagram illustrating another example electric configuration of a conventional endoscope system.

DETAILED DESCRIPTION OF THE PREFERRED EMBODIMENTS

Embodiments of the present invention will be described below with reference to the drawings.

<First Embodiment>

Figure 1:
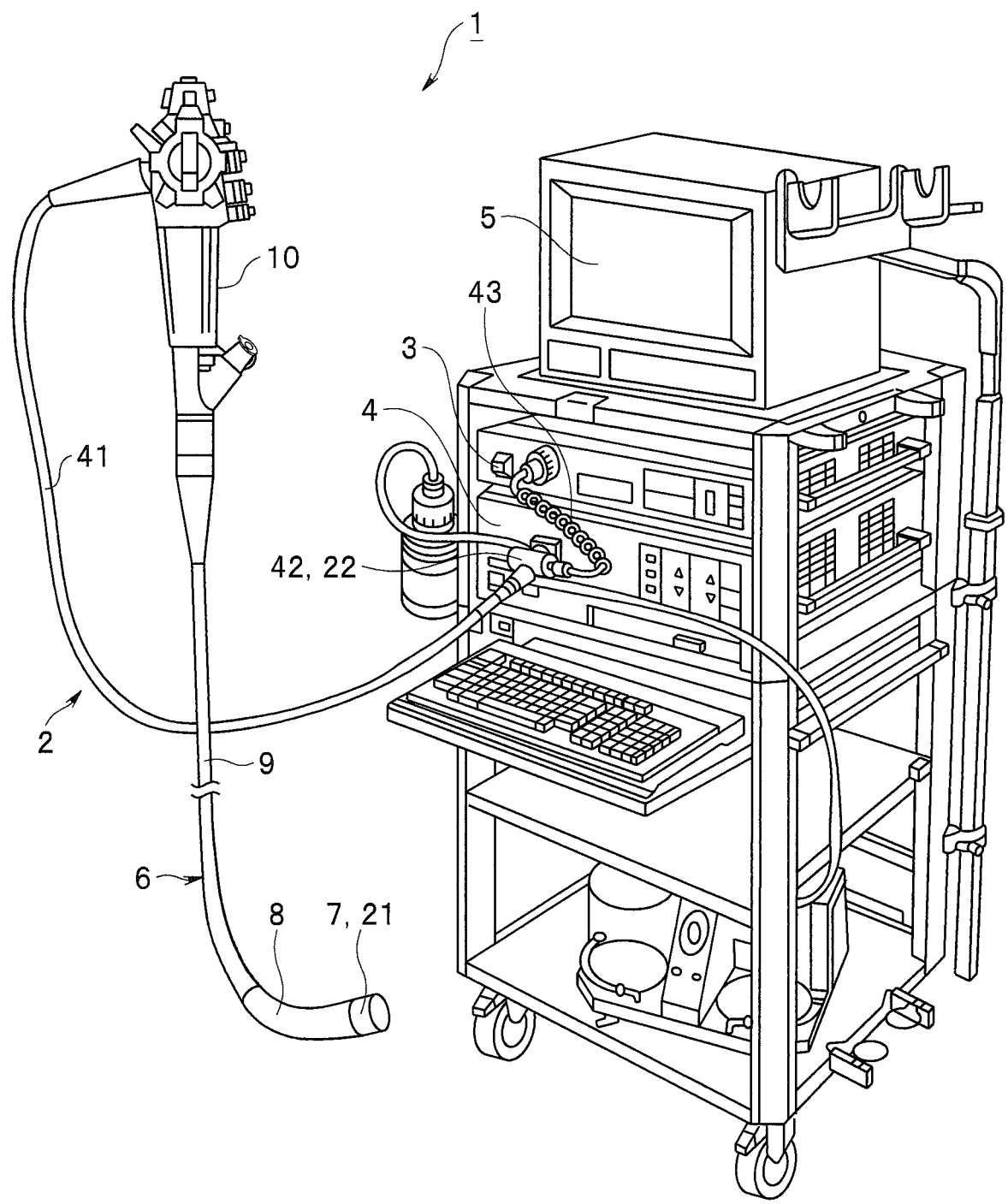
FIG. 1 is a diagram illustrating a configuration of an endoscope system according to a first embodiment of the present invention.
Figure 2:
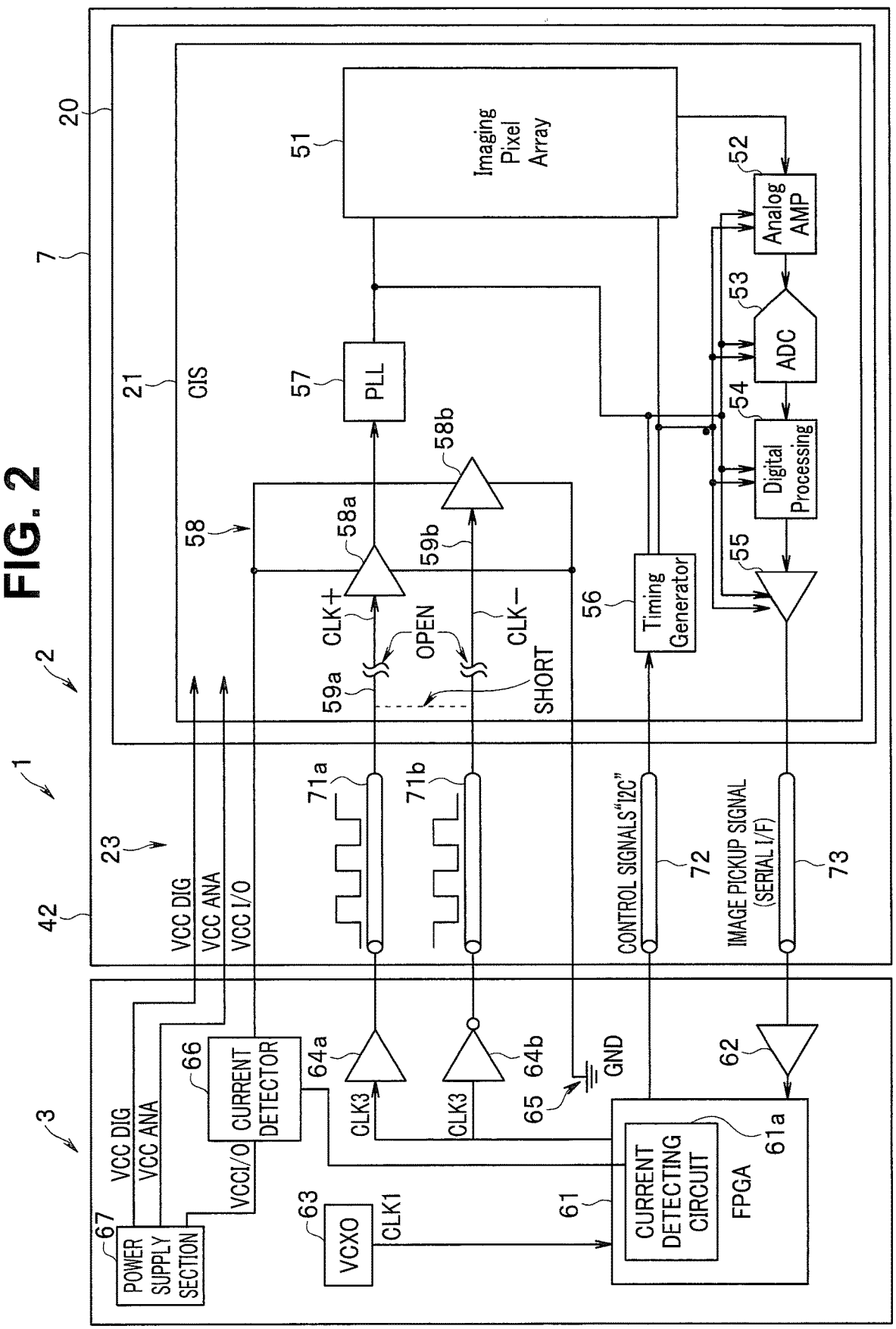
FIG. 2 is a block diagram illustrating schematic electric configurations of an endoscope and a video processor in the endoscope system according to the first embodiment.
Figure 3:
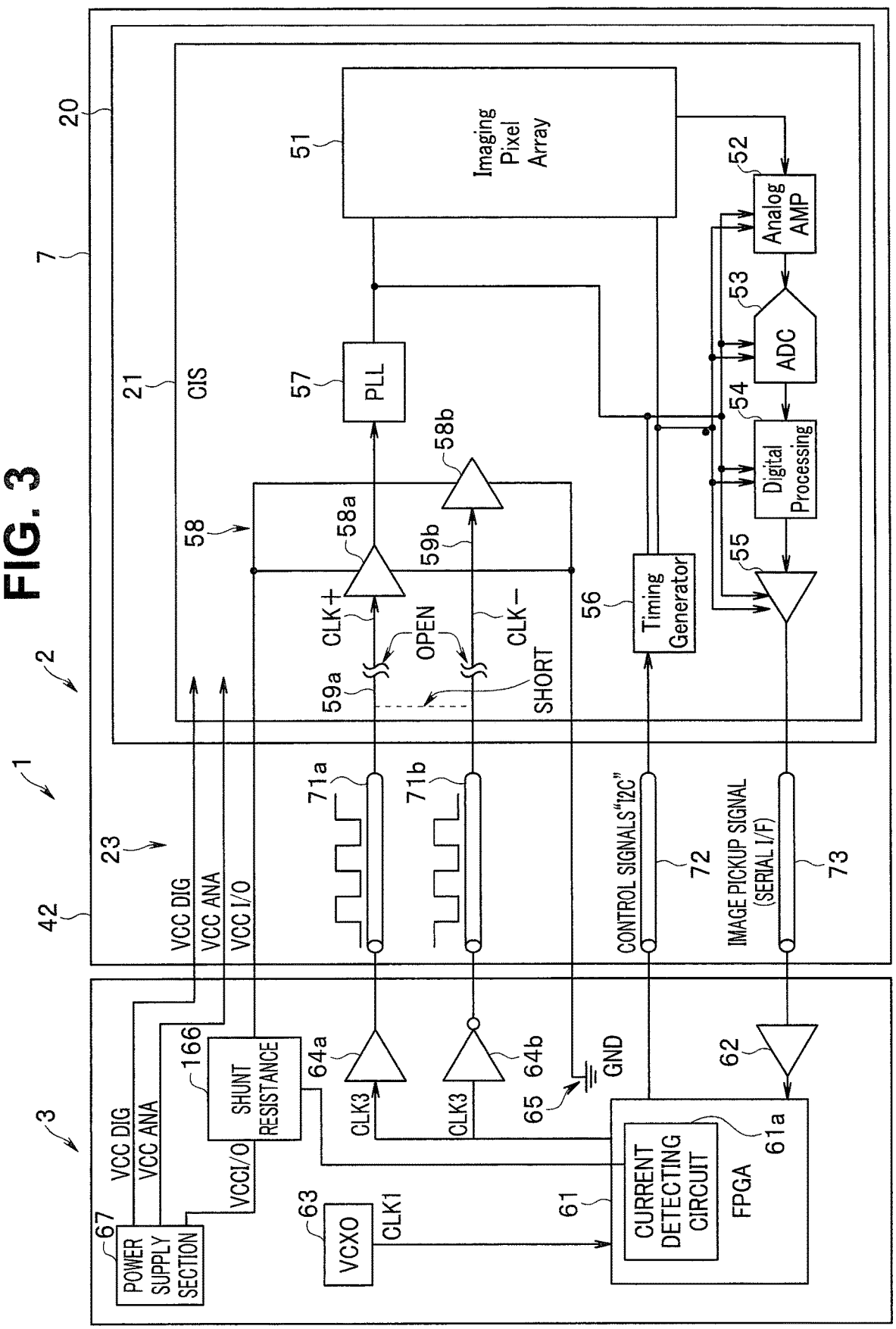
FIG. 3 is a block diagram illustrating schematic electric configurations of an endoscope and a video processor in the endoscope system according to the first embodiment.

FIG. 1 is a diagram illustrating a configuration of an endoscope system according to a first embodiment of the present invention, FIG. 2 is a block diagram illustrating schematic electric configurations of an endoscope and a video processor in the endoscope system according to the first embodiment, and FIG. 3 is a block diagram illustrating electric configurations of an endoscope and a video processor in the endoscope system according to the first embodiment.

As illustrated in FIGS. 1 and 2, an endoscope system 1 according to the first embodiment includes: an endoscope 2 configured to allow observation of a subject and pick up an image of the subject; a video processor 3 connected to the endoscope 2, the video processor 3 being a signal processing apparatus configured to receive an input of a signal of the image pickup and subject the image pickup signal to predetermined image processing; a light source apparatus 4 configured to supply illuminating light for illuminating the subject; and a monitor apparatus 5 configured to display an observation image according to the image pickup signal.

The endoscope 2 includes an elongated insertion portion 6 to be inserted into, e.g., a body cavity of a subject, an endoscope operation portion 10 disposed on the proximal end side of the insertion portion 6, the endoscope operation portion 10 to be grasped and operated by a surgeon, and a universal cord 41 including one end portion provided so as to extend from a side portion of the endoscope operation portion 10.

The insertion portion 6 includes a rigid distal end portion 7 provided on the distal end side, a bendable bending portion 8 provided at a rear end of the distal end portion 7, and a flexible tube portion 9 provided at a rear end of the bending portion 8, the flexible tube portion 9 having a long length and flexibility.

A connector 42 is provided on the proximal end side of the universal cord 41 and the connector 42 is connected to the light source apparatus 4. In other words, a sleeve (not illustrated), which is a connection end portion of a fluid conduit projecting from a distal end of the connector 42, and a light guide sleeve (not illustrated), which is an illuminating light supply end portion, are detachably connected to the light source apparatus 4.

Furthermore, one end of a connection cable 43 is connected at an electric contact portion provided at a side face of the connector 42. Inside the connection cable 43, for example, a signal wire configured to transmit an image pickup signal from an image pickup device 21 (see FIG. 2) in the endoscope 2 is provided, and a connector portion at the other end of the connection cable 43 is connected to the video processor 3.

In the connector 42, a connector circuit 22 including, e.g., a storage section (not illustrated) that stores predetermined ID information unique to the endoscope 2 (not illustrated) is disposed.

Also, in the distal end portion 7 of the insertion portion 6, an objective optical system (not illustrated) including a lens that allows entrance of light of an object image, an image pickup device 21 arranged at an image plane of the objective optical system, and an image pickup substrate 20 including the image pickup device 21 are disposed.

Furthermore, in the endoscope 2, a cable 23 (see FIG. 2) provided so as to extend from the image pickup device 21 to the connector 42 via the insertion portion 6, the operation portion 10 and the universal cord 41 is disposed.

Electric configurations of the endoscope 2 and the video processor 3 in the endoscope system 1 according to the present first embodiment will be described below with reference to FIGS. 2 and 3.

As illustrated in FIG. 2, the endoscope 2 includes the connector circuit 22 (not illustrated) provided inside the connector 42 connected to the video processor 3, the image pickup device 21 disposed in the distal end portion 7 of the insertion portion 6 of the endoscope 2, and the cable 23 connecting the connector circuit 22 and the image pickup device 21 disposed on the image pickup substrate 20.

As the image pickup device 21 in the present embodiment, a solid-state image pickup device configured by a CMOS (complementary metal-oxide semiconductor) image sensor is employed.

The cable 23 is provided so as to extend from the image pickup device 21 to the connector circuit 22 in the connector 42 via the insertion portion 6, the operation portion 10 and the universal cord 41 (see FIG. 1).

Here, the cable 23 internally holds a first clock signal wire 71a configured to transmit a first differential clock signal (CLK+), which is one of two differential clock signals transmitted from the video processor 3, and a second clock signal wire 71b configured to transmit a second differential clock signal (CLK−), which is the other of the two differential clock signals.

The first clock signal wire 71a connects a first clock signal output section 64a disposed in the video processor 3 and a first buffer 58a in a clock input section 58 of the image pickup device 21. The first clock signal output section 64*a*, the clock input section 58 and the first buffer 58*a* will be described in detail later.

Also, the second clock signal wire 71*b* connects a second clock signal output section 64*b* disposed in the video processor 3 and a second buffer 58*b* in the clock input section 58 of the image pickup device 21. The second clock signal output section 64*b*, the clock input section 58 and the second buffer 58*b* will be described in detail later.

The cable 23 internally holds various types of channels of power supply from the video processor 3 to the image pickup device 21 (a digital power supply channel VCCDIG, an analog power supply channel VCCANA and an I/O power supply channel VCCI/O in the present embodiment), a control signal wire 72 and an image pickup signal wire 73 (the control signal wire 72 and the image pickup signal wire 73 will be described later) in addition to the first clock signal wire 71*a* and the second clock signal wire 71*b*.

The image pickup device 21 includes an image pickup section 51 (denoted as Imaging Pixel Array in FIG. 2) including photo diodes (PD), which are a plurality of photoelectric conversion sections each configured to subject incident light to photoelectric conversion to generate signal charge.

Furthermore, the image pickup device 21 includes the clock input section 58 connected to the first clock signal wire 71*a* and the second clock signal wire 71*b* inside the cable 23, a PLL (phase locked loop) 57 connected to an output end of the clock input section 58, and a timing generator 56 connected to the control signal wire 72 inside the cable 23.

As described above, the clock input section 58 includes the first buffer 58*a* to which the first clock signal wire 71*a* is connected and the second buffer 58*b* to which the second clock signal wire 71*b* is connected.

Also, predetermined power (power supply voltage VCCI/O) is supplied to the first buffer 58*a* and the second buffer 58*b* via the I/O power supply channel VCCI/O from among various types of channels of power supply from the video processor 3.

The first clock signal wire 71*a* and the second clock signal wire 71*b* are provided so as to extend as a first clock signal line 59*a* (CLK+) and a second clock signal line 59*b* (CLK−) inside the image pickup device 21, respectively, and are connected to respective input ends of the first buffer 58*a* and the second buffer 58*b*.

Here, the clock input section 58 (the first buffer 58*a* and the second buffer 58*b*) serves as a clock receiving section, which is a clock receiving circuit, configured to receive two differential clock signals transmitted from the video processor 3.

In the image pickup device 21, the PLL 57 is what is called a phase synchronizing circuit, and is configured to multiply inputted clocks by predetermined times in the clock input section 58 and supply the resulting clocks to respective sections inside the image pickup device 21 in addition to the above-described image pickup section 51.

The timing generator 56 is configured to receive control signals transmitted via the control signal wire 72 inside the cable 23 (drive signal such as a vertical synchronization signal and a horizontal synchronization signal), generate predetermined timing pulse signals and supply the predetermined timing pulse signals to the respective sections inside the image pickup device 21 in addition to the image pickup section 51. In the present embodiment, the control signals are transmitted by what is called I2C (inter-integrated circuit).

On the other hand, the image pickup device 21 includes an AFE (analog front-end) connected to an output of the image pickup section 51. The AFE includes, e.g., an analog amplifier section (analog amp) 52 and an AD conversion section (ADC) 53 in addition to a non-illustrated CDS (correlated double sampling) circuit, and is controlled by timing pulse signals from the timing generator 56 and converts analog image pickup signals from the image pickup section 51 into digital signals.

Furthermore, the image pickup device 21 includes a digital processing section (digital processing) 54 configured to subject digital image pickup signals resulting from AD conversion by the AFE to predetermined processing, and a P/S conversion section 55 configured to convert parallel image pickup signals outputted from the digital processing section 54 into a predetermined serial signal.

A serial image pickup signal, which is a signal resulting from parallel/serial conversion in the P/S conversion section 55, is transmitted toward an FPGA 61 in the video processor 3 via the image pickup signal wire 73 inside the cable 23.

The control signal wire 72 connects the FPGA 61 (which will be described later) in the video processor 3 and the timing generator 56 in the image pickup device 21, and the image pickup signal wire 73 connects an S/P conversion section 62 in the video processor 3 and the P/S conversion section 55 in the image pickup device 21.

On the other hand, the video processor 3 has a function that generates the above-described differential clock signals and control signals, such as the synchronization signals, for driving the image pickup device 21 disposed in the distal end portion 7 of the insertion portion, and includes the FPGA 61, a crystal oscillator (VCXO) 63, the first clock signal output section 64*a* and the second clock signal output section 64*b*.

Also, the video processor 3 includes a power supply section 67, which is a power supply, for supplying power to various types of circuits in addition to supplying predetermined drive power to the image pickup device 21 in the endoscope 2.

Furthermore, the video processor 3 includes a current detector 66 disposed on the high side of the power supply channel (VCCI/O) for supplying predetermined drive power to the clock input section 58, the power supply channel (VCCI/O) being an output end of the power supply section 67, and a ground end 65 of the power supply channel.

The crystal oscillator VCXO (voltage-controlled crystal oscillator) 63 (hereinafter VCXO 63) is a voltage-controlled crystal oscillator and is configured to generate and output predetermined first clocks CLK1.

The current detector 66 configures a part of a current detecting section, which is a current detecting circuit, configured to detect a current value relating to the drive power supplied from the power supply section 67 to the clock receiving section (clock input section 58) via the power supply channel (VCCI/O).

Also, in the present first embodiment, more specifically, the current detector 66 is configured by a shunt resistance 166 as illustrated in FIG. 3. The shunt resistance 166 is configured by, for example, a resistance exhibiting a resistance value of several tens to several hundreds of milliohms, and is serially inserted in the relevant power supply channel (VCCI/O) from the power supply section 67.

Also, both ends of the shunt resistance 166 are connected to the current detecting circuit 61*a* in the FPGA 61 so that a voltage drop value, that is, a current value, of the shunt resistance 166 is detected by the current detecting circuit 61*a*.

The FPGA 61 is configured by what is called an FPGA (field programmable gate array) and has a function that controls various circuits in the video processor 3 and the endoscope 2 in addition to functions such as driving of the image pickup device 21 and processing of image pickup signals from the image pickup device 21.

First, the FPGA 61 has a function that receives an input of a first clock signal (CLK1) generated by the VCXO 63 and generates a clock signal (second clocks CLK3) in order to drive the image pickup device 21.

Here, the FPGA 61 includes a non-illustrated PLL (phase locked loop) circuit. Then, the PLL circuit receives first clocks CLK1 from the VCXO 63 and outputs CLK2 obtained as a result of the first clock being multiplied by predetermined times.

The FPGA 61 further subjects CLK2 to predetermined processing to generate a clock signal (second clocks CLK3) for driving the image pickup device 21 and outputs the clock signal (second clocks CLK3) to the first clock signal output section 64a and the second clock signal output section 64b.

The FPGA 61 constitutes a part of a differential signal output section, which is a differential signal output circuit, configured to receive an input of a first clock signal generated by the VCXO 63 and converts the first clock signal into two differential clock signals, respective phases of which are reverse of each other, and outputs the two differential clock signals.

Furthermore, the FPGA 61 configures a current detecting section, as a current detecting circuit, in which the current detecting circuit 61a connected to the current detector 66 is formed, the current detecting section being configured to detect a current value relating to the drive power supplied to the clock receiving section (clock input section 58) from the power supply section 67 via the relevant power supply channel (VCCI/O) in cooperation with the current detector 66.

Furthermore, the FPGA 61 forms a failure mode determining section, which is a failure mode determining apparatus, configured to, based on the current value detected by the current detecting circuit 61a (current detecting section), determine a failure state relating to at least one of the first clock signal wire 71a and the second clock signal wire 71b in the endoscope.

More specifically, first, the "failure mode determining section" in the FPGA 61 is capable of determining whether or not a shorted state occurs between the first clock signal wire 71a and the second clock signal wire 71b (or a shorted state occurs between the first clock signal line 59a and the second clock signal line 59b).

Furthermore, the "failure mode determining section" in the FPGA 61 is capable of determining whether or not an open state occurs in the first clock signal wire 71a or the second clock signal wire 71b (or an open state occurs in the first clock signal line 59a or the second clock signal line 59b).

Note that the function of the "failure mode determining section" as the failure mode determining apparatus may be executed by a software. For example, the "failure mode determining section" including a hardware includes a central processing unit (CPU), ROM, RAM, etc., and a program corresponding to the function stored in the ROM may be read out and executed by the CPU.

In addition, the FPGA 61 is configured to form, e.g., a function that generates control signals such as various synchronization signals as a master in I2C transmission and a video processing function for digital image pickup signals inputted from the image pickup device 21.

As described above, each of the first clock signal output section 64a and the second clock signal output section 64b receives an input of second clocks CLK3 from the FPGA 61.

Then, the first clock signal output section 64a outputs the second clocks CLK3 toward the first clock signal wire 71a in the form of a first differential clock signal (CLK+). On the other hand, the second clock signal output section 64b is configured by an inverter and outputs a clock signal resulting from the second clocks CLK3 being reversed, toward the second clock signal wire 71b as a second differential clock signal (CLK−).

Here, the first differential clock signal (CLK+) and the second differential clock signal (CLK−) are clock signals, respective phases of which are reverse of each other and respective DC bias levels of which are set to be equal to each other.

In other words, in the present embodiment, in the first clock signal wire 71a and the second clock signal wire 71b, differential clock signals are transmitted in a differential manner.

The FPGA 61 configures a part of a differential signal output section, which is a differential signal output circuit, configured to receive an input of a generated first clock signal and convert the first clock signal into two differential clock signals, respective phases of which are reverse of each other, and output the two differential clock signals.

The S/P conversion section 62 has a serial/parallel conversion function that converts a serial digital image pickup signal inputted via the image pickup signal wire 73 into predetermined parallel signals.

Next, operation of the present embodiment will be described.

<Short Between the First Clock Signal Wire and the Second Clock Signal Wire>

As described above, the first differential clock signal (CLK+) transmitted in the first clock signal wire 71a (first clock signal line 59a) and the second differential clock signal (CLK−) transmitted in the second clock signal wire 71b (second clock signal line 59b) are clock signals, respective DC bias levels of which are set to be equal to each other and respective phases of which are reverse of each other.

Here, it is assumed that a short occurs between the first clock signal line 59a in the first clock signal wire 71a and the second clock signal line 59b in the second clock signal wire 71b (see FIGS. 2 and 3).

In this case, since the DC bias levels of the first differential clock signal (CLK+) and the second differential clock signal (CLK−) are set to be equal to each other, for example, current consumption does not substantially change in the first clock signal output section 64a and the second clock signal output section 64b. Also, in the first clock signal line 59a and the second clock signal line 59b, the first differential clock signal (CLK+) and the second differential clock signal (CLK−) both exhibit a characteristic of an amplitude of the clock signal being lost or significantly attenuated.

In this case, in the first buffer 58a and the second buffer 58b, the inputted first differential clock signal (CLK+) and the inputted second differential clock signal (CLK−) both continue staying at around a common level, and thus respective flow-through currents in the buffers themselves become large.

In other words, this means that a current value of the current in the VCCI/O channel, which is supplied to the first buffer 58a and the second buffer 58b, becomes large.

In the present embodiment, the current value of the current flowing in the VCCI/O channel is measured and detected by the current detector 66 (shunt resistance 166 in the present embodiment) inserted in the VCCI/O channel and the current detecting circuit 61a in the FPGA 61.

Furthermore, based on the current value detected in the current detecting circuit 61a (current detecting section), the "failure mode determining section" formed in the FPGA 61 determines whether or not a shorted state occurs between the first clock signal line 59a (first clock signal wire 71a) and the second clock signal line 59b (second clock signal wire 71b).

<Open in the First Clock Signal Wire or the Second Clock Signal Wire>

Here, it is assumed that an open occurs in either the first clock signal line 59a in the first clock signal wire 71a or the second clock signal line 59b in the second clock signal wire 71b (see FIGS. 2 and 3).

In this case, in the first buffer 58a or the second buffer 58b on the open-occurrence side, an input continues staying at an intermediate node or at around a self-bias, and thus, also as in the case of the short above, a flow-through current in the buffer on the open-occurrence side itself becomes large.

In other words, as in the above, this means that a current value of the current in the VCCI/O channel, which is supplied to the first buffer 58a or the second buffer 58b, becomes large.

Then, as in the above, the current value of the current flowing in the VCCI/O channel is measured and detected by the current detector 66 (shunt resistance 166 in the present embodiment) inserted in the VCCI/O channel and the current detecting circuit 61a in the FPGA 61.

Furthermore, based on the current value detected by the current detecting circuit 61a (current detecting section), the "failure mode determining section" formed in the FPGA 61 determines whether or not an open state occurs in the first clock signal line 59a (first clock signal wire 71a) or the second clock signal line 59b (second clock signal wire 71b).

As described above, according to the present embodiment, the differential clock signals (the first differential clock signal (CLK+) and the second differential clock signal (CLK−)) transmitted in the first and second clock signal wires 71a, 71b (first and second clock signal lines 59a, 59b) are not directly monitored, but the current value of the current in the supply line (VCCI/O) of power (power supply voltage) for driving the clock input sections 58a, 58b of the image pickup device 21, which are input sections for the differential clock signals, is detected, enabling accurate detection of a failure (a short or an open) in the differential clock signals transmitted from the signal processing apparatus (video processor 3) to the image pickup device 21 of the endoscope 2.

<Second Embodiment>

Next, a second embodiment of the present invention will be described.

Figure 4:
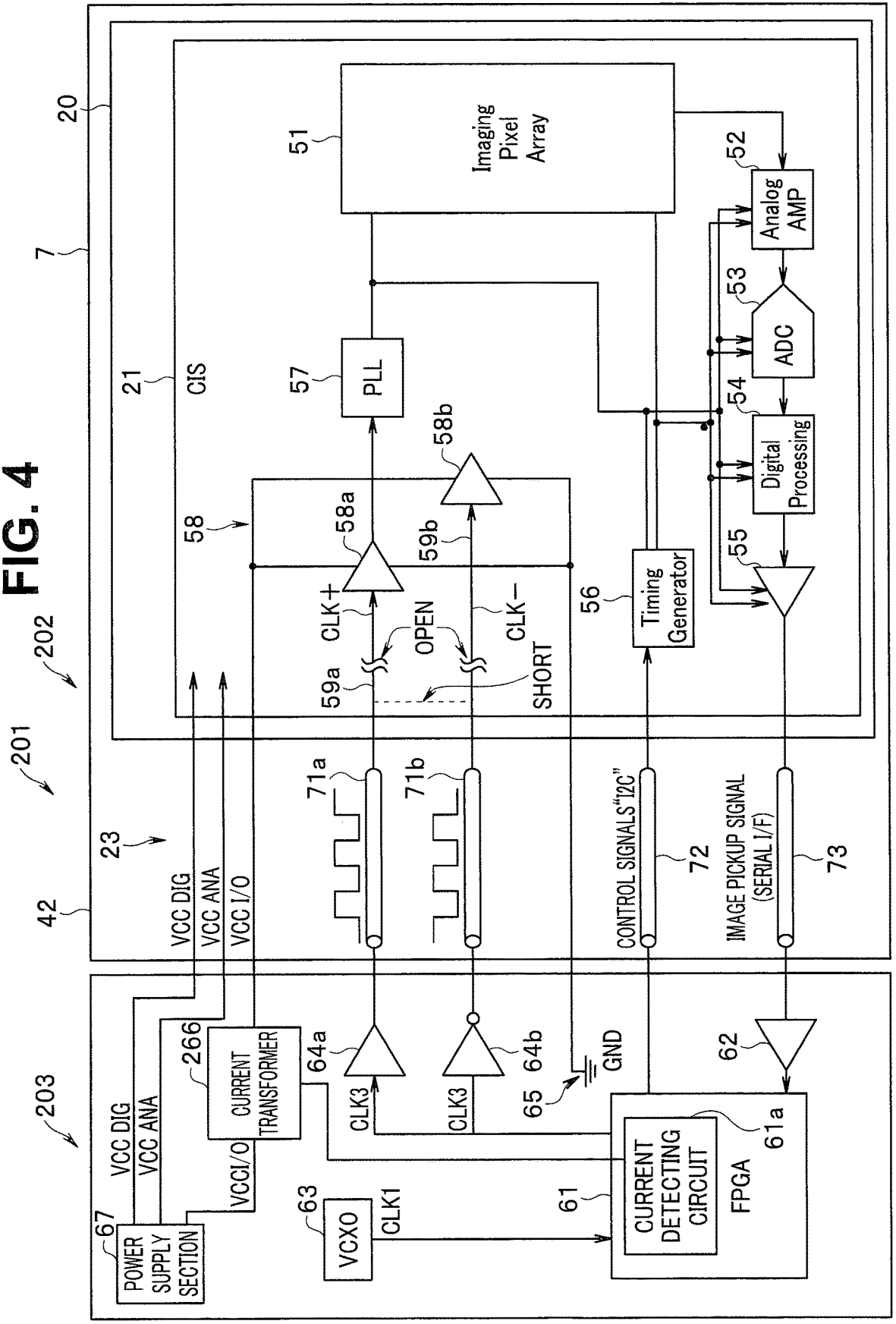
FIG. 4 is a block diagram illustrating schematic electric configurations of an endoscope and a video processor in an endoscope system according to a second embodiment of the present invention.

FIG. 4 is a block diagram illustrating electric configurations of an endoscope and a video processor in an endoscope system according to a second embodiment of the present invention.

The endoscope system according to the second embodiment is similar in basic configuration to the first embodiment but is different in configuration of the current detector 66 from the first embodiment.

Therefore, here, only differences from the first embodiment will be described and description of parts in common with the first embodiment will be omitted.

As illustrated in FIG. 4, an endoscope system 201 according to the second embodiment includes, instead of the current detector 66 in the first embodiment, a current transformer 266 disposed in a VCCI/O channel from a power supply section 67 in a video processor 203 connected to an endoscope 202.

The current transformer 266 is configured by a hollow coil obtained by an electric wire being wounded around a ferromagnetic core material, and is capable of measuring a current in a measurement target signal wire in cooperation with a current detecting circuit 61a by the signal wire being inserted into a hollow part. In other words, the current transformer 266 is capable of measuring and detecting a current value of current flowing in a signal wire without being in contact with the signal wire.

In the second embodiment, also, as in the above-described first embodiment, a current value of current flowing in the VCCI/O channel is measured and detected by the current transformer 266 inserted in the VCCI/O channel and the current detecting circuit 61a in an FPGA 61.

Then, as in the first embodiment, based on the current value detected by the current detecting circuit 61a (current detecting section), the above-described "failure mode determining section" formed in the FPGA 61 determines whether or not a shorted state occurs between a first clock signal line 59a (first clock signal wire 71a) and a second clock signal line 59b (second clock signal wire 71b) or an open state occurs in the first clock signal line 59a (first clock signal wire 71a) or the second clock signal line 59b (second clock signal wire 71b).

As described above, according to the second embodiment, as in the first embodiment, differential clock signals (a first differential clock signal (CLK+) and a second differential clock signal (CLK−)) transmitted in the first and second clock signal wires 71a, 71b (first and second clock signal lines 59a, 59b) are not directly monitored, but the current value of the current in the supply line (VCCI/O) of power for driving clock input sections 58a, 58b of an image pickup device 21, which are input sections for the differential clock signals, is detected, enabling accurate detection of a failure (a short or an open) in the differential clock signals transmitted from the signal processing apparatus (video processor 203) to the image pickup device 21 of the endoscope 202.

<Third Embodiment>

Next, a third embodiment of the present invention will be described.

Figure 5:
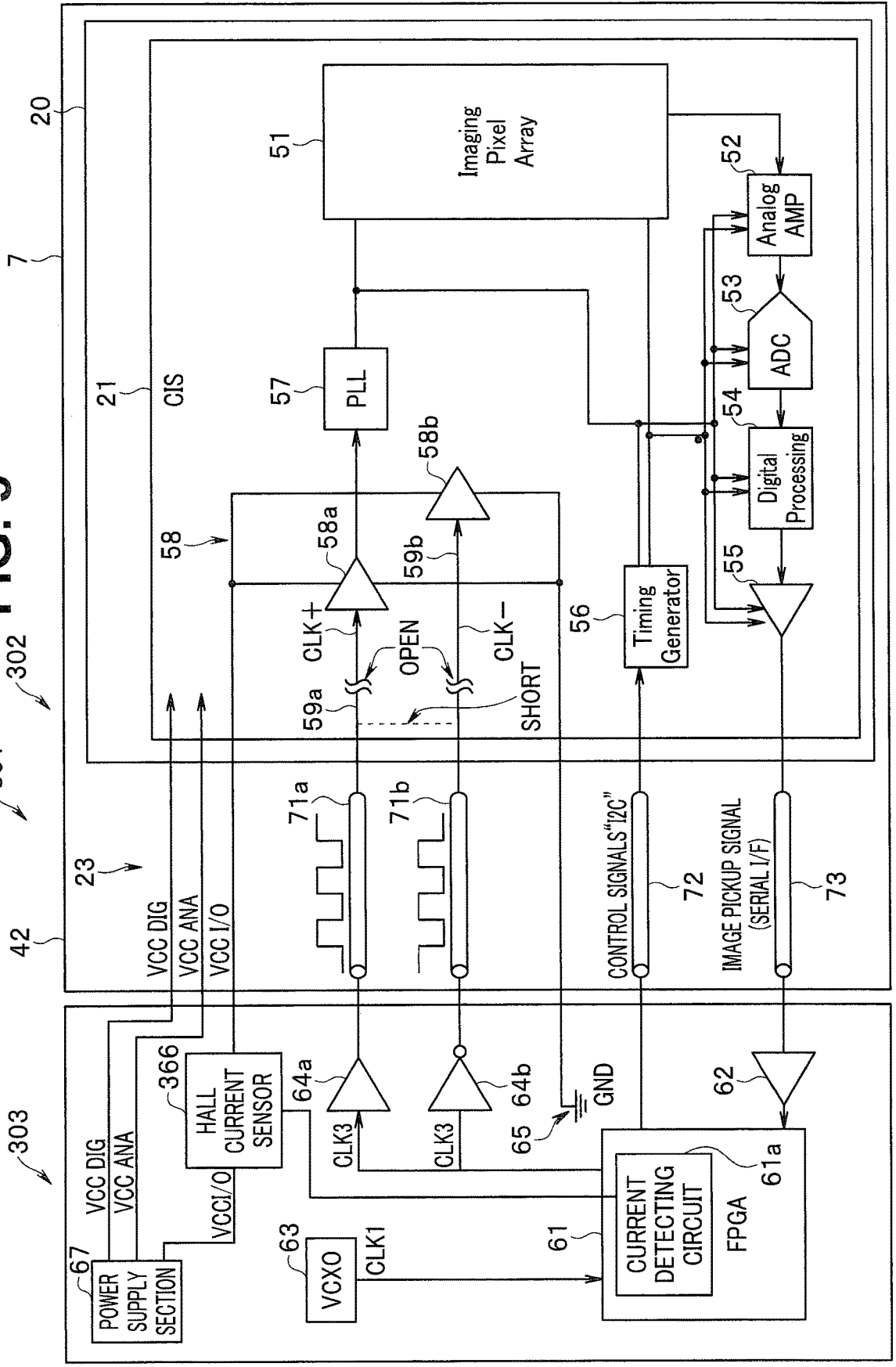
FIG. 5 is a block diagram illustrating schematic electric configurations of an endoscope and a video processor in an endoscope system according to a third embodiment of the present invention.

FIG. 5 is a block diagram illustrating electric configurations of an endoscope and a video processor in an endoscope system according to a third embodiment of the present invention.

The endoscope system according to the third embodiment is similar in basic configuration to the first embodiment but is different in configuration of the current detector 66 from the first embodiment.

Therefore, here, only differences from the first embodiment will be described and description of parts in common with the first embodiment will be omitted.

As illustrated in FIG. 5, in an endoscope system 301 according to the third embodiment includes, instead of the current detector 66 in the first embodiment, a Hall current sensor 366 disposed in a VCCI/O channel from a power supply section 67 in a video processor 303 connected to an endoscope 302.

The Hall current sensor 366 is a sensor configured to measure a magnetic flux density proportional to a current to be measured, and is capable of measuring a current in a relevant signal wire in cooperation with a current detecting circuit 61a connected to the Hall current sensor 366. In other words, as in the second embodiment, the Hall current sensor 366 is also capable of measuring and detecting a current value of current flowing in a signal wire without being in contact with the signal wire.

In the third embodiment, also, as in the above-described first and second embodiments, a current value of current flowing in the VCCI/O channel is measured and detected by the Hall current sensor 366 inserted in the VCCI/O channel and the current detecting circuit 61a in an FPGA 61.

Then, as in the first embodiment, based on the current value detected by the current detecting circuit 61a (current detecting section), the above-described "failure mode determining section" formed in the FPGA 61 determines whether or not a shorted state occurs between a first clock signal line 59a (first clock signal wire 71a) and a second clock signal line 59b (second clock signal wire 71b) or an open state occurs in the first clock signal line 59a (first clock signal wire 71a) or the second clock signal line 59b (second clock signal wire 71b).

As described above, according to the third embodiment, as in the first and second embodiments, differential clock signals (a first differential clock signal (CLK+) and a second differential clock signal (CLK−)) transmitted in the first and second clock signal wires 71a, 71b (first and second clock signal lines 59a, 59b) are not directly monitored, but the current value of the current in the supply line (VCCI/O) of power for driving clock input sections 58a, 58b of an image pickup device 21, which are input sections for the differential clock signals, is detected, enabling accurate detection of a failure (a short or an open) in the differential clock signals transmitted from the signal processing apparatus (video processor 303) to the image pickup device 21 of the endoscope 302.

<Fourth Embodiment>

Next, a fourth embodiment of the present invention will be described.

Figure 6:
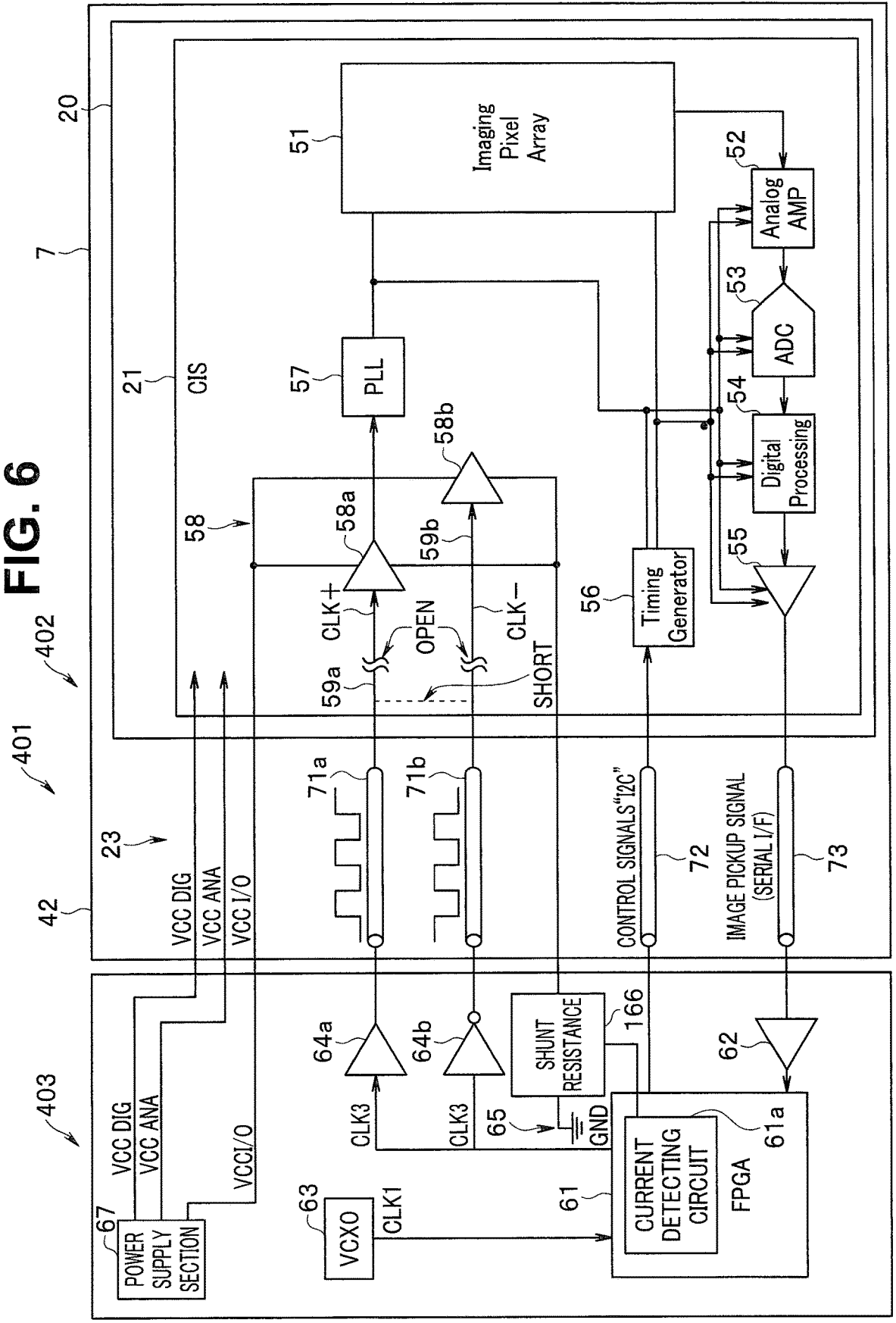
FIG. 6 is a block diagram illustrating schematic electric configurations of an endoscope and a video processor in an endoscope system according to a fourth embodiment of the present invention.

FIG. 6 is a block diagram illustrating electric configurations of an endoscope and a video processor in an endoscope system according to a fourth embodiment of the present invention.

The endoscope system according to the fourth embodiment is similar in basic configuration to the first embodiment but is different in position where the current detector 66 is disposed from the first embodiment.

Therefore, here, only differences from the first embodiment will be described and description of parts in common with the first embodiment will be omitted.

As described above, in the first embodiment, the current detector 66 (shunt resistance 166) is inserted on the high side of the VCCI/O channel of an output from the power supply section 67. On the other hand, as illustrated in FIG. 6, an endoscope system 401 according to the fourth embodiment includes a shunt resistance 466 inserted on the ground side of a VCCI/O channel in a video processor 403 connected to an endoscope 402.

The fourth embodiment configured as above also exerts operation and effects similar to the operation and the effects of the above-described first embodiment.

<Fifth Embodiment>

Next, a fifth embodiment of the present invention will be described.

Figure 7:
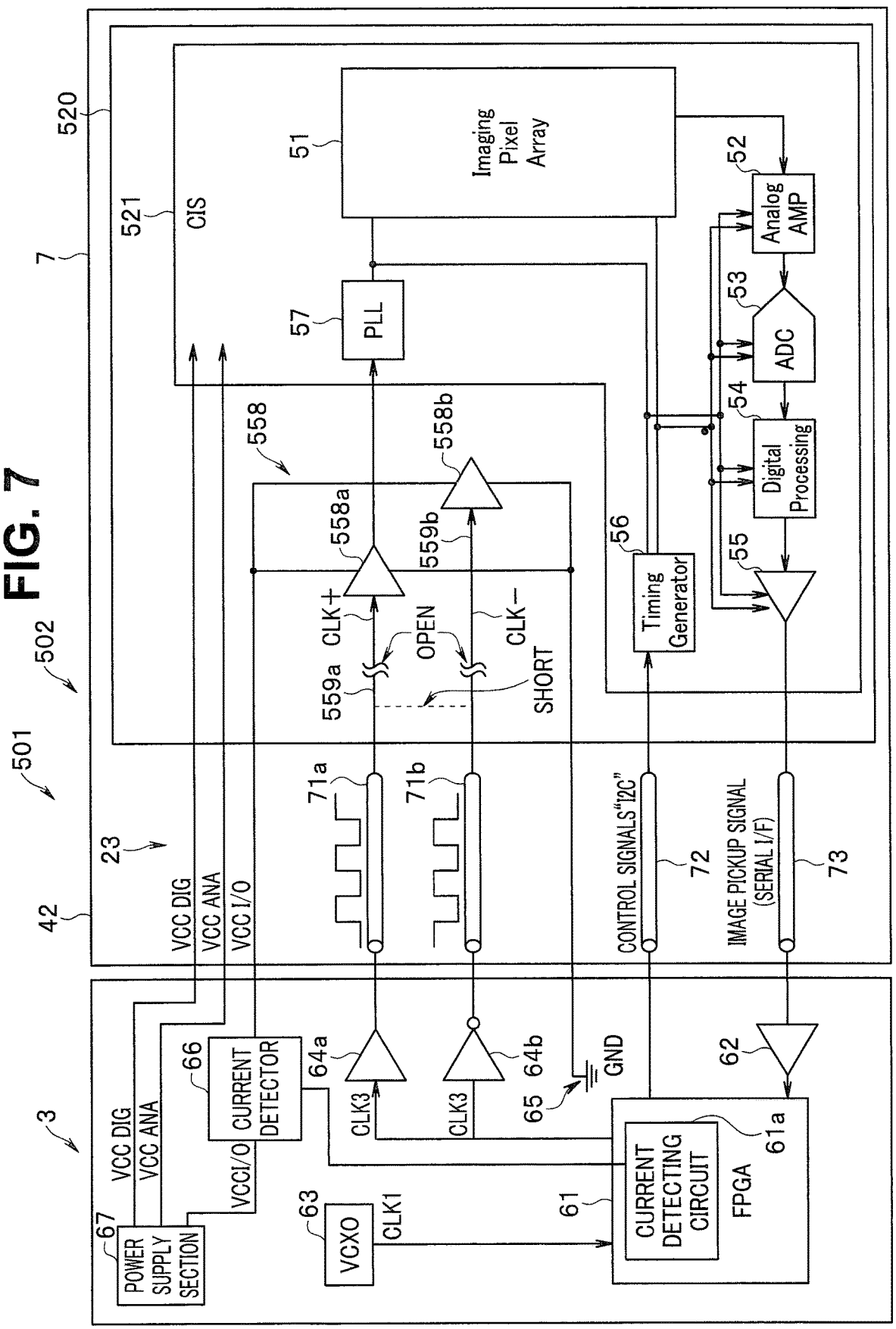
FIG. 7 is a block diagram illustrating schematic electric configurations of an endoscope and a video processor in an endoscope system according to a fifth embodiment of the present invention.

FIG. 7 is a block diagram illustrating electric configurations of an endoscope and a video processor in an endoscope system according to a fifth embodiment of the present invention.

The endoscope system according to the fifth embodiment is similar in basic configuration to the first embodiment but is different in site at which the clock input section 58 is disposed from the first embodiment.

Therefore, here, only differences from the first embodiment will be described and description of parts in common with the first embodiment will be omitted.

As described above, the endoscope system 1 according to the first embodiment includes the clock input section 58 provided inside the image pickup device 21. On the other hand, as illustrated in FIG. 7, an endoscope system 501 according to the fifth embodiment includes a clock input section 558 disposed outside an image pickup device 521, the clock input section 558 having a configuration that is similar to the configuration of the clock input section 58.

In other words, the endoscope system 501 according to the fifth embodiment includes an image pickup substrate 520 disposed in a distal end portion 7 of an endoscope 502. Then, the image pickup device 521 and the clock input section 558, which is a clock input section for the image pickup device 521, are disposed on the image pickup substrate 520.

The configuration of the clock input section 558 is similar to the configuration of the clock input section 58 in the first embodiment and operation of the clock input section 558 is similar to the operation of the clock input section 58.

The clock input section 558 in the fifth embodiment will be described in detail below.

In the fifth embodiment, as in the first embodiment, the clock input section 558 includes a first buffer 558a to which a first clock signal wire 71a is connected and a second buffer 558b to which a second clock signal wire 71b are connected.

In the fifth embodiment, also, predetermined power (power supply voltage VCCI/O) is supplied to the first buffer 558a and the second buffer 558b via an I/O power supply channel VCCI/O from among various types of channels of power supply from a video processor 3.

The first clock signal wire 71a and the second clock signal wire 71b are provided so as to extend as a first clock signal line 559a (CLK+) and a second clock signal line 559b (CLK−) inside the image pickup substrate 520, respectively, and are connected to respective input ends of the first buffer 558a and the second buffer 558b.

Here, as in the first embodiment, the clock input section 558 (the first buffer 558a and the second buffer 558b) serves a clock receiving section configured to receive two differential clock signals transmitted from the video processor 3.

In the endoscope system 501 according to the fifth embodiment, an image pickup section 51, an analog amplifier section 52, an AD conversion section 53, a digital processing section 54, a P/S conversion section 55, a timing generator 56, a PLL 57, etc., in the image pickup device 521 are similar in configuration and operation to the image pickup section 51, the analog amplifier section 52, the AD conversion section 53, the digital processing section 54, the P/S conversion section 55, the timing generator 56, the PLL 57, etc., in the first embodiment, and thus, detailed description of such configurations and operation will be omitted here.

Also, a configuration and operation of the video processor 3 are similar to the configuration and operation of the video processor 3 in the first embodiment and thus detailed description of such configuration and operation will be omitted here; however, in the fifth embodiment, also, first, the "failure mode determining section" in an FPGA 61 is capable of determining whether or not a shorted state occurs between the first clock signal wire 71a and the second clock signal wire 71b (or a shorted state occurs between the first clock signal line 559a and the second clock signal line 559b).

Furthermore, in the fifth embodiment, the "failure mode determining section" in the FPGA 61 is capable of determining whether or not an open state occurs in the first clock signal wire 71*a* or the second clock signal wire 71*b* (or an open state occurs in the first clock signal line 559*a* or the second clock signal line 559*b*).

Next, operation of the fifth embodiment will be described.
<Short Between the First Clock Signal Wire and the Second Clock Signal Wire>

As described above, also in the fifth embodiment, a first differential clock signal (CLK+) transmitted in the first clock signal wire 71*a* (first clock signal line 559*a*) and a second differential clock signal (CLK−) transmitted in the second clock signal wire 71*b* (second clock signal line 559*b*) are clock signals, respective DC bias levels of which are set to be equal to each other and respective phases of which are reverse of each other.

Here, it is assumed that a short occurs between the first clock signal line 559*a* in the first clock signal wire 71*a* and the second clock signal line 559*b* in the second clock signal wire 71*b* (see FIG. 7).

In this case, since the DC bias levels of the first differential clock signal (CLK+) and the second differential clock signal (CLK−) are set to be equal to each other, for example, current consumption does not substantially change in a first clock signal output section 64*a* and a second clock signal output section 64*b*. Also, in the first clock signal line 559*a* and the second clock signal line 559*b*, the first differential clock signal (CLK+) and the second differential clock signal (CLK−) both exhibit a characteristic of an amplitude of the clock signal being lost or significantly attenuated.

In this case, in the first buffer 558*a* and the second buffer 558*b*, the inputted first differential clock signal (CLK+) and the inputted second differential clock signal (CLK−) both continue staying at around a common level, and thus respective flow-through currents in the buffers themselves become large.

In other words, this means that a current value of current in the VCCI/O channel, which is supplied to the first buffer 558*a* and the second buffer 558*b*, becomes large.

In the fifth embodiment, also, the current value of the current flowing in the VCCI/O channel is measured and detected by a current detector 66 (for example, a shunt resistance 166) inserted in the VCCI/O channel and a current detecting circuit 61*a* in the FPGA 61.

Furthermore, based on the current value detected in the current detecting circuit 61*a* (current detecting section), the above-described "failure mode determining section" formed in the FPGA 61 determines whether or not a shorted state occurs between the first clock signal line 559*a* (first clock signal wire 71*a*) and the second clock signal line 559*b* (second clock signal wire 71*b*).
<Open in the First Clock Signal Wire or the Second Clock Signal Wire>

Here, it is assumed that an open occurs in either the first clock signal line 559*a* in the first clock signal wire 71*a* or the second clock signal line 559*b* in the second clock signal wire 71*b* (see FIG. 7).

In this case, in the first buffer 558*a* or the second buffer 558*b* on the open-occurrence side, an input continues staying at an intermediate node or at around a self-bias, and thus, also as in the case of the short above, a flow-through current in the buffer on the open-occurrence side itself becomes large.

In other words, as in the above, this means that a current value of the current in the VCCI/O channel, which is supplied to the first buffer 558*a* or the second buffer 558*b*, becomes large.

Then, as in the above, the current value of the current flowing in the VCCI/O channel is measured and detected by the current detector 66 (for example, the shunt resistance 166) inserted in the VCCI/O channel and the current detecting circuit 61*a* in the FPGA 61.

Furthermore, based on the current value detected by the current detecting circuit 61*a* (current detecting section), the above-described "failure mode determining section" formed in the FPGA 61 determines whether or not an open state occurs in the first clock signal line 559*a* (first clock signal wire 71*a*) or the second clock signal line 559*b* (second clock signal wire 71*b*).

As described above, according to the fifth embodiment, as in the first embodiment, the differential clock signals (the first differential clock signal (CLK+) and the second differential clock signal (CLK−)) transmitted in the first and second clock signal wires 71*a*, 71*b* (first and second clock signal lines 559*a*, 559*b*) are not directly monitored, but the current value of the current in the supply line (VCCI/O) of power for driving the first buffer 558*a* and the second buffer 558*b*, which are input sections for the differential clock signals, is detected, enabling accurate detection of a failure (a short or an open) in the differential clock signals transmitted from the signal processing apparatus (video processor 3) to the image pickup device 521 of the endoscope 502.
<Sixth Embodiment>

Next, a sixth embodiment of the present invention will be described.

Figure 8:
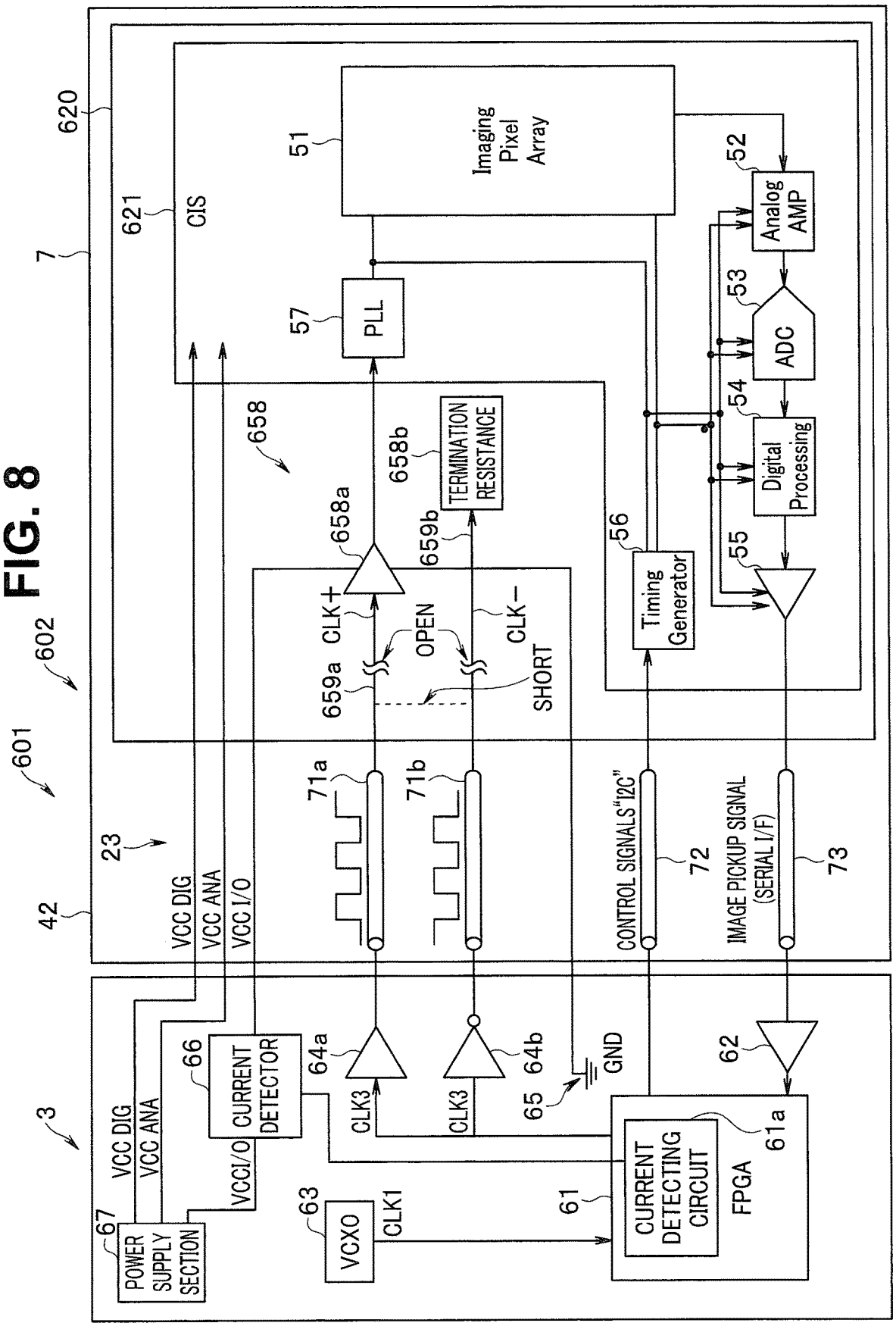
FIG. 8 is a block diagram illustrating schematic electric configurations of an endoscope and a video processor in an endoscope system according to a sixth embodiment of the present invention.

FIG. 8 is a block diagram illustrating electric configurations of an endoscope and a video processor in an endoscope system according to a sixth embodiment of the present invention.

The endoscope system according to the sixth embodiment is similar in basic configuration to the first embodiment but is different in configuration of the clock input section 58 from the first embodiment.

Therefore, here, only differences from the first embodiment will be described and description of parts in common with the first embodiment will be omitted.

As described above, the endoscope system 1 according to the first embodiment includes the clock input section 58 provided inside the image pickup device 21. On the other hand, as illustrated in FIG. 8, an endoscope system 601 according to the sixth embodiment first includes a clock input section 658 disposed outside an image pickup device 621, the clock input section 658 being configured to receive an input of clocks to be supplied to the image pickup device 621.

In other words, the endoscope system 601 according to the sixth embodiment includes an image pickup substrate 620 disposed in a distal end portion 7 of an endoscope 602. Then, the image pickup device 621 and the clock input section 658, which is a clock input section for the image pickup device 621, are disposed on the image pickup substrate 620.

The clock input section 658 in the sixth embodiment will be described in detail below.

In the sixth embodiment, the clock input section 658 includes a first buffer 658*a* to which a first clock signal wire 71*a* is connected and a termination resistance 658*b* to which a second clock signal wire 71*b* are connected.

Also, predetermined power (power supply voltage VCCI/O) is supplied to the first buffer 658*a* via an I/O power supply channel VCCI/O from among various types of channels of power supply from a video processor 3.

The first clock signal wire 71a and the second clock signal wire 71b are provided so as to extend as a first clock signal line 659a (CLK+) and a second clock signal line 659b (CLK−) inside the image pickup substrate 620, respectively, and are connected to the first buffer 658a and the termination resistance 658b, respectively.

Here, as in the first embodiment, the clock input section 658 (the first buffer 658a and the termination resistance 658b) serves as a clock receiving section configured to receive two differential clock signals transmitted from the video processor 3.

In the endoscope system 601 according to the sixth embodiment, an image pickup section 51, an analog amplifier section 52, an AD conversion section 53, a digital processing section 54, a P/S conversion section 55, a timing generator 56, a PLL 57, etc., in the image pickup device 621 are similar in configuration and operation to the image pickup section 51, the analog amplifier section 52, the AD conversion section 53, the digital processing section 54, the P/S conversion section 55, the timing generator 56, the PLL 57, etc., in the first embodiment, and thus, detailed description of such configurations and operation will be omitted here.

Also, a configuration and operation of the video processor 3 are similar to the configuration and operation of the video processor 3 in the first embodiment and thus detailed description of such configuration and operation will be omitted here; however, in the sixth embodiment, also, first, the "failure mode determining section" in an FPGA 61 is capable of determining whether or not a shorted state occurs between the first clock signal wire 71a and the second clock signal wire 71b (or a shorted state occurs between the first clock signal line 659a and the second clock signal line 659b).

Furthermore, in the sixth embodiment, the "failure mode determining section" in the FPGA 61 is capable of determining whether or not an open state occurs in the first clock signal wire 71a or the second clock signal wire 71b (or an open state occurs in the first clock signal line 659a or the second clock signal line 659b).

Next, operation of the sixth embodiment will be described.

<Short Between the First Clock Signal Wire and the Second Clock Signal Wire>

As described above, also in the sixth embodiment, a first differential clock signal (CLK+) transmitted in the first clock signal wire 71a (first clock signal line 659a) and a second differential clock signal (CLK−) transmitted in the second clock signal wire 71b (second clock signal line 659b) are clock signals, respective DC bias levels of which are set to be equal to each other and respective phases of which are reverse of each other.

Here, it is assumed that a short occurs between the first clock signal line 659a in the first clock signal wire 71a and the second clock signal line 659b in the second clock signal wire 71b (see FIG. 8).

In this case, since the DC bias levels of the first differential clock signal (CLK+) and the second differential clock signal (CLK−) are set to be equal to each other, for example, current consumption does not substantially change in a first clock signal output section 64a and a second clock signal output section 64b. Also, in the first clock signal line 659a and the second clock signal line 659b, the first differential clock signal (CLK+) and the second differential clock signal (CLK−) both exhibit a characteristic of an amplitude of the clock signal being lost or significantly attenuated.

In this case, in the first buffer 658a, the inputted first differential clock signal (CLK+) continues staying at around a common level, and thus a flow-through current in the buffer itself becomes large.

In other words, this means that a current value of current in the VCCI/O channel, which is supplied to the first buffer 658a, becomes large.

In the sixth embodiment, also, the current value of the current flowing in the VCCI/O channel is measured and detected by a current detector 66 (for example, a shunt resistance 166) inserted in the VCCI/O channel and a current detecting circuit 61a in the FPGA 61.

Furthermore, in the sixth embodiment, also, based on the current value detected in the current detecting circuit 61a (current detecting section), the above-described "failure mode determining section" formed in the FPGA 61 determines whether or not a shorted state occurs between the first clock signal line 659a (first clock signal wire 71a) and the second clock signal line 659b (second clock signal wire 71b).

<Open in the First Clock Signal Wire or the Second Clock Signal Wire>

Here, it is assumed that an open occurs in either the first clock signal line 659a in the first clock signal wire 71a or the second clock signal line 659b in the second clock signal wire 71b (see FIG. 8).

In this case, in the first buffer 658a, an input continues staying at an intermediate node or around a self-bias, and thus, also as in the case of the short above, a flow-through current in the first buffer 658a itself becomes large.

In other words, as in the above, this means that a current value of the current in the VCCI/O channel, which is supplied to the first buffer 658a, becomes large.

Then, as in the above, the current value of the current flowing in the VCCI/O channel is measured and detected by the current detector 66 (for example, the shunt resistance 166) inserted in the VCCI/O channel and the current detecting circuit 61a in the FPGA 61.

Furthermore, based on the current value detected by the current detecting circuit 61a (current detecting section), the above-described "failure mode determining section" formed in the FPGA 61 determines whether or not an open state occurs in the first clock signal line 659a (first clock signal wire 71a) or the second clock signal line 659b (second clock signal wire 71b).

As described above, according to the sixth embodiment, as in the first embodiment, the differential clock signals (the first differential clock signal (CLK+) and the second differential clock signal (CLK−)) transmitted in the first and second clock signal wires 71a, 71b (first and second clock signal lines 659a, 659b) are not directly monitored, but the current value of the current in the supply line (VCCI/O) of power for driving the first buffer 658a, which is an input section for the relevant differential clock signal, is detected, enabling accurate detection of a failure (a short or an open) in the differential clock signals transmitted from the signal processing apparatus (video processor 3) to the image pickup device 621 of the endoscope 602.

<Seventh Embodiment>

Next, a seventh embodiment of the present invention will be described.

Figure 9:
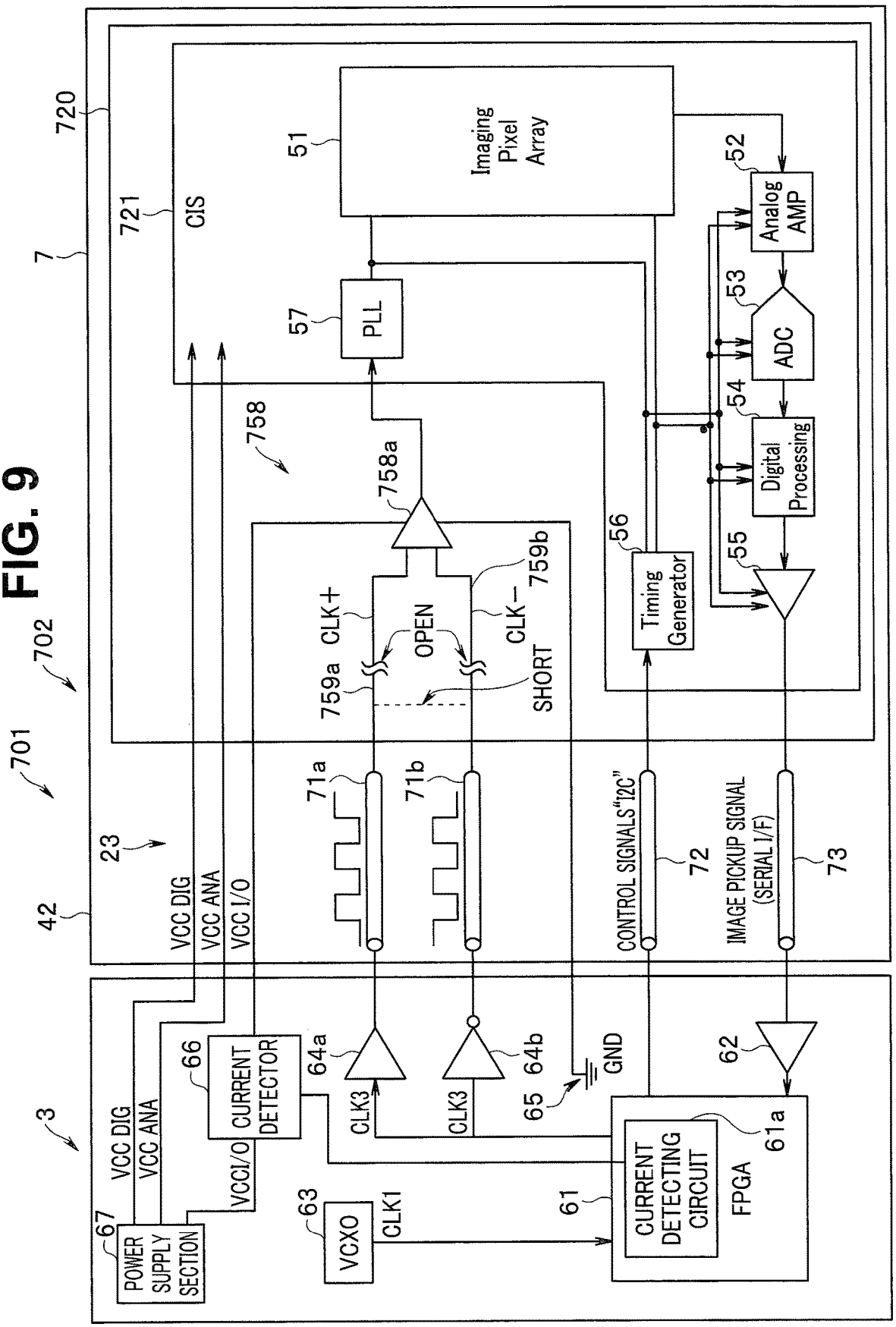
FIG. 9 is a block diagram illustrating schematic electric configurations of an endoscope and a video processor in an endoscope system according to a seventh embodiment of the present invention.
Figure 10:
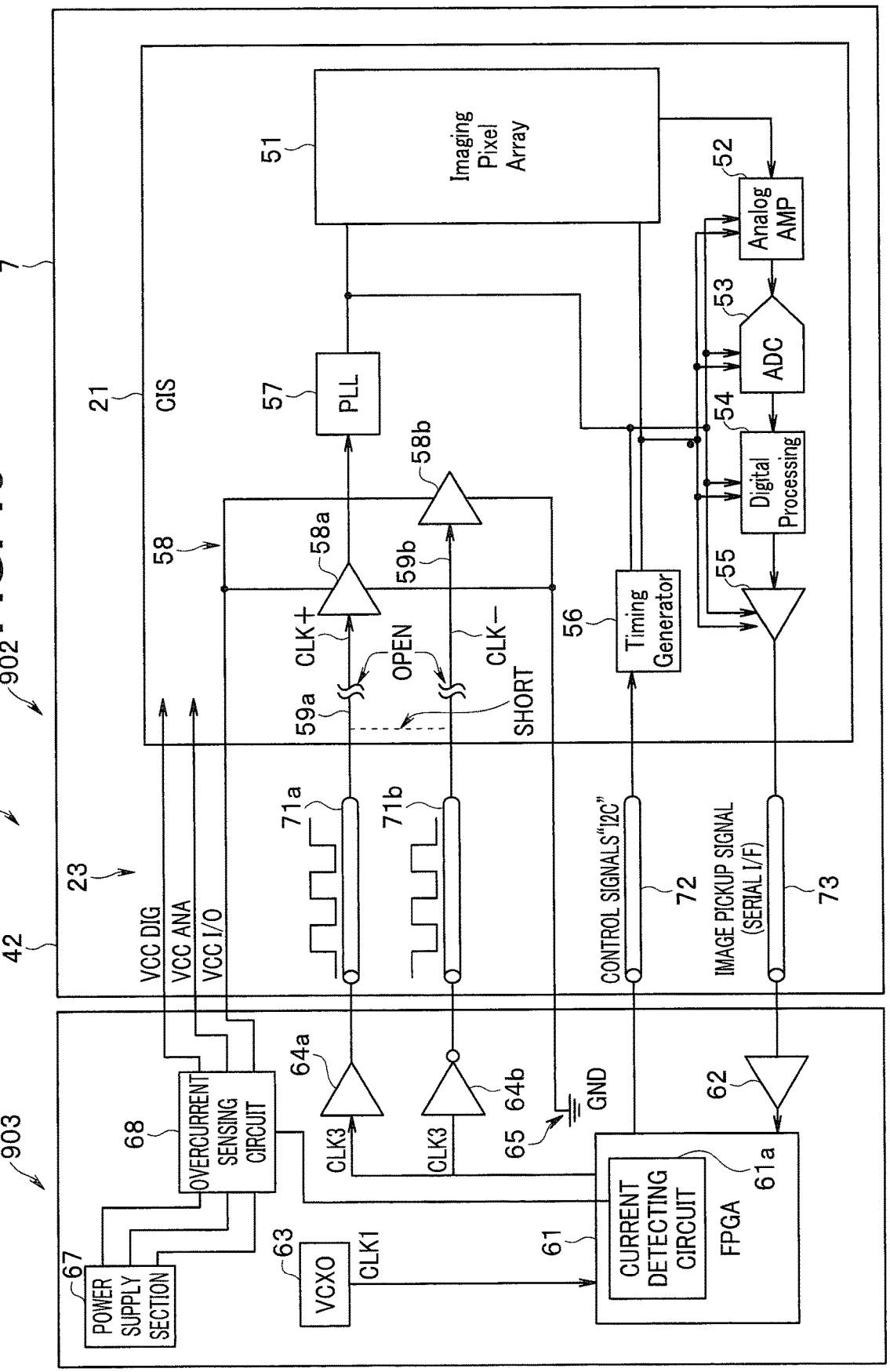
FIG. 10 is a block diagram illustrating an example electric configuration of a conventional endoscope system.

FIG. 9 is a block diagram illustrating electric configurations of an endoscope and a video processor in an endoscope system according to a seventh embodiment of the present invention.

The endoscope system according to the seventh embodiment is similar in basic configuration to the first embodiment but is different in configuration of the clock input section 58 from the first embodiment.

Therefore, here, only differences from the first embodiment will be described and description of parts in common with the first embodiment will be omitted.

As described above, the endoscope system 1 according to the first embodiment includes the clock input section 58 provided inside the image pickup device 21. On the other hand, as illustrated in FIG. 9, an endoscope system 701 according to the seventh embodiment includes a clock input section 758 disposed outside an image pickup device 721, the clock input section 758 being configured to receive an input of clocks to be supplied to the image pickup device 721.

In other words, the endoscope system 701 according to the seventh embodiment includes an image pickup substrate 720 disposed in a distal end portion 7 of an endoscope 702. Then, the image pickup device 721 and the clock input section 758, which is a clock input section for the image pickup device 721, are disposed on the image pickup substrate 720.

The clock input section 758 in the seventh embodiment will be described in detail below.

In the seventh embodiment, the clock input section 758 includes a differential amplifier 758a configured to receive inputs from a first clock signal wire 71a and a second clock signal wire 71b.

In the seventh embodiment, predetermined power (power supply voltage VCCI/O) is supplied to the differential amplifier 758a via an I/O power supply channel VCCI/O from among various types of channels of power supply from a video processor 3.

The first clock signal wire 71a and the second clock signal wire 71b are provided so as to extend as a first clock signal line 759a (CLK+) and a second clock signal line 759b (CLK−) inside the image pickup substrate 720, respectively, and are connected to respective input ends of the differential amplifier 758a.

Also, an output end of the differential amplifier 758a is connected to an input end of a PLL 57 in the image pickup device 721 and an output of the differential amplifier 758a is inputted to the PLL 57.

Here, as in the first embodiment, the clock input section 758 (differential amplifier 758a) serves a clock receiving section configured to receive two differential clock signals transmitted from the video processor 3.

In the endoscope system 701 according to the seventh embodiment, an image pickup section 51, an analog amplifier section 52, an AD conversion section 53, a digital processing section 54, a P/S conversion section 55, a timing generator 56, the PLL 57, etc., in the image pickup device 721 are similar in configuration and operation to the image pickup section 51, the analog amplifier section 52, the AD conversion section 53, the digital processing section 54, the P/S conversion section 55, the timing generator 56, the PLL 57, etc., in the first embodiment, and thus, detailed description of such configurations and operation will be omitted here.

Also, a configuration and operation of the video processor 3 are similar to the configuration and operation of the video processor 3 in the first embodiment and thus detailed description of such configuration and operation will be omitted here; however, in the seventh embodiment, also, first, the "failure mode determining section" in an FPGA 61 is capable of determining whether or not a shorted state occurs between the first clock signal wire 71a and the second clock signal wire 71b (or a shorted state occurs between the first clock signal line 759a and the second clock signal line 759b).

Furthermore, in the seventh embodiment, the "failure mode determining section" in the FPGA 61 is capable of determining whether or not an open state occurs in the first clock signal wire 71a or the second clock signal wire 71b (or an open state occurs in the first clock signal line 759a or the second clock signal line 759b).

Next, operation of the seventh embodiment will be described.

<Short Between the First Clock Signal Wire and the Second Clock Signal Wire>

As described above, also in the seventh embodiment, a first differential clock signal (CLK+) transmitted in the first clock signal wire 71a (first clock signal line 759a) and a second differential clock signal (CLK−) transmitted in the second clock signal wire 71b (second clock signal line 759b) are clock signals, respective DC bias levels of which are set to be equal to each other and respective phases of which are reverse of each other.

Here, it is assumed that a short occurs between the first clock signal line 759a in the first clock signal wire 71a and the second clock signal line 759b in the second clock signal wire 71b (see FIG. 9).

In this case, since the DC bias levels of the first differential clock signal (CLK+) and the second differential clock signal (CLK−) are set to be equal to each other, for example, current consumption does not substantially change in a first clock signal output section 64a and a second clock signal output section 64b. Also, in the first clock signal line 759a and the second clock signal line 759b, the first differential clock signal (CLK+) and the second differential clock signal (CLK−) both exhibit a characteristic of an amplitude of the clock signal being lost or significantly attenuated.

In this case, in the differential amplifier 758a, the inputted first differential clock signal (CLK+) and the inputted second differential clock signal (CLK−) both continue staying at around a common level, and thus a flow-through current in the amplifier (buffer) itself becomes large.

In other words, this means that a current value of current in the VCCI/O channel, which is supplied to the differential amplifier 758a becomes large.

In the seventh embodiment, also, the current value of the current flowing in the VCCI/O channel is measured and detected by a current detector 66 (for example, a shunt resistance 166) inserted in the VCCI/O channel and a current detecting circuit 61a in the FPGA 61.

Furthermore, based on the current value detected in the current detecting circuit 61a (current detecting section), the above-described "failure mode determining section" formed in the FPGA 61 determines whether or not a shorted state occurs between the first clock signal line 759a (first clock signal wire 71a) and the second clock signal line 759b (second clock signal wire 71b).

<Open in the First Clock Signal Wire or the Second Clock Signal Wire>

Here, it is assumed that an open occurs in either the first clock signal line 759a in the first clock signal wire 71a or the second clock signal line 759b in the second clock signal wire 71b (see FIG. 9).

In this case, in the differential amplifier 758a, either of inputs continues staying at an intermediate node or at around a self-bias, and thus, also as in the case of the short above, a flow-through current in an input buffer on the open-occurrence side itself becomes large.

In other words, as in the above, this means that a current value of the current in the VCCI/O channel, which is supplied to the differential amplifier 758*a*, becomes large.

Then, as in the above, the current value of the current flowing in the VCCI/O channel is measured and detected by the current detector 66 (for example, the shunt resistance 166) inserted in the VCCI/O channel and the current detecting circuit 61*a* in the FPGA 61.

Furthermore, based on the current value detected by the current detecting circuit 61*a* (current detecting section), the above-described "failure mode determining section" formed in the FPGA 61 determines whether or not an open state occurs in the first clock signal line 759*a* (first clock signal wire 71*a*) or the second clock signal line 759*b* (second clock signal wire 71*b*).

As described above, according to the seventh embodiment, as in the first embodiment, the differential clock signals (the first differential clock signal (CLK+) and the second differential clock signal (CLK−)) transmitted in the first and second clock signal wires 71*a*, 71*b* (first and second clock signal lines 759*a*, 759*b*) are not directly monitored, but the current value of the current in the supply line (VCCI/O) of power for driving the differential amplifier 758*a*, which is an input section for the relevant differential clock signal, is detected, enabling accurate detection of a failure (a short or an open) in the differential clock signals transmitted from the signal processing apparatus (video processor 3) to the image pickup device 721 of the endoscope 702.

In each of the above-described embodiments, the FPGA 61 is disposed in the video processor 3, and the present invention is not limited to this case and the FPGA 61 may be provided inside the connector circuit 22 in the endoscope.

The present invention enables provision of an endoscope system and a signal processing apparatus that enable a failure state in a transmission path of a clock signal supplied to an image pickup device to be detected without the clock signal transmission path being directly subjected to measurement.

The present invention is not limited to the above-described embodiments and various changes, alterations, etc., are possible without departing from the spirit of the present invention.

What is claimed is:

1. An endoscope system comprising:
   an endoscope comprising:
      an image pickup sensor configured to be driven by a predetermined clock,
      a clock receiving circuit configured to receive two differential clock signals transmitted from external signal wires, phases of the two differential clock signals being reverse of each other
      a first clock signal wire configured to transmit a first differential clock signal that is one signal of the two differential clock signals, and
      a second clock signal wire configured to transmit a second differential clock signal that is another signal of the two differential clock signals; and
   a signal processor configured to:
      supply drive power to the clock receiving circuit via a predetermined power supply channel,
      detect a current value relating to the drive power supplied to the clock receiving circuit via the power supply channel,
      receive an input of a generated clock signal, convert the clock signal into the two differential clock signals, the phases of the two differential clock signals being reverse of each other, and output the two differential clock signals to the clock receiving circuit, and
      based on the detected current value, determine a failure state relating to at least one of the first clock signal wire and the second clock signal wire in the endoscope.

2. The endoscope system according to claim 1, wherein the determination of the failure state comprises determining whether or not a shorted state occurs between the first clock signal wire and the second clock signal wire in the endoscope.

3. The endoscope system according to claim 1, wherein the determination of the failure state comprises determining whether or not an open state occurs in the first clock signal wire or the second clock signal wire in the endoscope.

4. The endoscope system according to claim 1, wherein the determination of the failure state comprises determining whether or not a shorted state occurs between the first clock signal wire and the second clock signal wire in the endoscope or an open state occurs in the first clock signal wire or the second clock signal wire.

5. The endoscope system according to claim 1, further comprising a storage configured to store table information corresponding to the current value,
   wherein the signal processor matches the detected current value and the table information stored in the storage with each other to determine the failure state based on the table information corresponding to the current value.

6. The endoscope system according to claim 1, wherein the clock receiving circuit is provided in the image pickup sensor.

7. A signal processor for connection to an endoscope, the endoscope comprising an image pickup sensor configured to be driven by a predetermined clock, a clock receiving circuit configured to receive two differential clock signals transmitted from external signal wires, phases of the two differential clock signals being reverse of each other, a first clock signal wire configured to transmit a first differential clock signal that is one signal of the two differential clock signals, and a second clock signal wire configured to transmit a second differential clock signal that is another signal of the two differential clock signals, the signal processor being configured to:
   supply drive power to the clock receiving circuit via a predetermined power supply channel;
   detect a current value relating to the drive power supplied to the clock receiving circuit via the power supply channel;
   receive an input of a generated clock signal, convert the clock signal into the two differential clock signals, the phases of the two differential clock signals being reverse of each other, and output the two differential clock signals to the clock receiving circuit; and
   based on the detected current value, determine a failure state relating to at least one of the first clock signal wire and the second clock signal wire in the endoscope.

8. The signal processor according to claim 7, wherein the determination of the failure state comprises determining whether or not a shorted state occurs between the first clock signal wire and the second clock signal wire in the endoscope.

9. The signal processor according to claim 7, wherein the determination of the failure state comprises determining whether or not an open state occurs in the first clock signal wire or the second clock signal wire in the endoscope.

10. The signal processor according to claim 7, wherein the determination of the failure state comprises determining whether or not a shorted state occurs between the first clock signal wire and the second clock signal wire in the endoscope or an open state occurs in the first clock signal wire or the second clock signal wire.

11. The signal processor according to claim 7, further comprising a storage configured to store table information corresponding to the current value,
   wherein the signal processor matches the detected current value and the table information stored in the storage with each other to determine the failure state based on the table information corresponding to the current value.

12. The endoscope system according to claim 1, wherein the signal processor comprises a current detecting circuit for detecting the current value, the current detecting circuit comprising a hollow coil having an electric wire wound around a ferromagnetic core material, the current detecting circuit being configured to detect the current value supplied to the clock receiving circuit by the power supply channel being inserted into a hollow part.

13. The endoscope system according to claim 1, wherein the signal processor comprises a current detecting circuit for detecting the current value, the current detecting circuit comprising a sensor configured to measure a magnetic flux density proportional to a current flowing in the power supply channel.

14. The signal processor according to claim 7, wherein the signal processor comprises a current detecting circuit for detecting the current value, the current detecting circuit comprising a hollow coil having an electric wire wound around a ferromagnetic core material, the current detecting circuit being configured to detect the current value supplied to the clock receiving circuit by the power supply channel being inserted into a hollow part.

15. The signal processor according to claim 7, wherein the signal processor comprises a current detecting circuit for detecting the current value, the current detecting circuit comprising a sensor configured to measure a magnetic flux density proportional to a current flowing in the power supply channel.

* * * * *